United States Patent [19]
Kaliher et al.

[11] 3,952,748
[45] Apr. 27, 1976

[54] ELECTROSURGICAL SYSTEM PROVIDING A FULGURATION CURRENT

[75] Inventors: Paul L. Kaliher, White Bear Lake; Fred W. Nelson, Cottage Grove; Bryan K. Roos, North St. Paul, all of Minn.

[73] Assignee: Minnesota Mining and Manufacturing Company, St. Paul, Minn.

[22] Filed: July 18, 1974

[21] Appl. No.: 489,519

[52] U.S. Cl. .................... 128/303.14; 128/303.17; 307/112; 323/45
[51] Int. Cl.² .................... A61B 17/36; A61N 3/02
[58] Field of Search .................. 128/303.14, 303.17, 128/303.13, 303.18; 307/112; 323/45

[56] References Cited
UNITED STATES PATENTS

| | | | |
|---|---|---|---|
| 1,841,968 | 1/1932 | Lowry | 128/303.14 |
| 3,058,470 | 10/1962 | Seeliger | 128/303.14 |
| 3,478,744 | 11/1969 | Leiter | 128/303.14 |
| 3,730,188 | 5/1973 | Ellman | 128/303.17 |
| 3,804,096 | 4/1974 | Gonser | 128/303.14 |
| 3,875,945 | 4/1975 | Friedman | 128/303.17 |

Primary Examiner—Robert W. Michell
Assistant Examiner—Lee S. Cohen
Attorney, Agent, or Firm—Alexander, Sell, Steldt & DeLaHunt

[57] ABSTRACT

An electrosurgical system, having a solid state generator for providing a cut mode electrosurgical current waveform of RF electric energy having a first voltage amplitude to an active electrode terminal, is adapted by the addition of an apparatus for alternatively providing a fulguration mode current waveform having a second higher voltage amplitude from the generator to the active electrode terminal. A fulguration adaptor including a transformer for enabling the generator to provide a fulguration mode waveform having said second higher voltage amplitude; switching apparatus connected to the transformer for selectively connecting the transformer to the generator for providing said fulguration mode waveform, for disconnecting the transformer from the generator, and for switching off the current from the generator when operated to disconnect the transformer; and a delay circuit connected to the switching apparatus for delaying said disconnection of the transformer until after the current from the generator has been switched off.

3 Claims, 7 Drawing Figures

ELECTROSURGICAL SYSTEM PROVIDING A FULGURATION CURRENT

BACKGROUND OF THE INVENTION

1. Field of the Invention

This invention is related to electrosurgical systems and more particularly to a solid state electrosurgical generator system suitable for generating cutting and fulgurating electrosurgical currents.

2. Discussion of the Prior Art

Electrosurgical systems have been used for surgical procedures since the early part of the twentieth century with only minor changes until the past several years. The unchanged basic principle lies in the fact that a radio-frequency, or RF, electrical current which oscillates in the range of 0.4 to 2.5 megahertz can be used to cut or sear flesh without disturbing the nerve functions of the patient or operator.

The RF current is generated by a generator in an electrosurgical system and fed to an active electrode which generates heat at the operating site when the active electrode is placed in contact with the patient. The circuit is completed through a portion of the patient to an indifferent or return electrode which is placed in contact with the patient to supply a return path for the current to the electrosurgical generator.

Electrosurgery is considered better than the conventional scalpel for operations involving tissues with oozing capillary beds, particularly in organs such as liver, spleen, thyroid and lung, because it can provide either simultaneous or sequential cutting and coagulation or hemostasis thereby providing faster and neater sectioning of these organs. Because of the increased operating speed in the hand of a skilled surgeon, electrosurgery is a preferred technique for organ transplants and for long involved operations.

The first application of RF current for electrosurgery in the early 1900's used a spark gap or Tesla coil to generate a "fulguration" current. The fulguration current involved a series of rapidly damped RF waves having an initial high voltage amplitude. While not useful for cutting flesh, the fulguration effect charred surrounding flesh, producing a coagulation or hemostasis effect over quite a broad surface.

Electrosurgical systems introduced later in the early part of this century used vacuum tubes to produce a RF current of steady or undamped amplitude for use in a cutting mode, hereinafter referred to as a "cut" current. Since the steady Rf output of the vacuum tubes had much lower peak voltage output, and much higher average power, these units were not useful for producing coagulation. For many years, the practical use of electrosurgery required the use of large bulky generators which combined the features of both a spark-gap RF generator and a vacuum tube type RF generator so that both a fulguration current and a cut current could be provided to the active electrode as needed.

Within the past several years many solid state electrosurgical systems have been developed. These contain compact RF generators of much improved reliability, efficiency and safety. These systems usually provide at least two separate and distinct RF current waveforms to the active electrode, to wit: a continuous undamped relatively low voltage cut mode current similar to that of the outdated vacuum tube generator and either a damped or interrupted (or damped and interupted) likewise low voltage current for use in coagulating mode, hereinafter referred to as a "coagulate" current.

Most of these solid state electrosurgical systems, such as those described in U.S. Pat. No. 3,675,655 to Sittner, and U.S. Pat. No. 3,699,967 to Anderson, are quite versatile, providing in addition to both a cutting mode and a coagulation mode, a combined cutting and coagulation mode wherein a "blend" current is provided. In spite of such versatility the new solid state electrosurgery systems have not been widely accepted because they do not provide a fulguration current as do the old bulky electrosurgical systems that the surgeon is familiar with. The coagulate current although somewhat similar to the fulguration current of the outdated spark gap units is at a lower peak voltage and hence the effect is different. Production of heat, either at the arc or in adjacent tissue, is a function of both current density and duration. The fulguration effect produced by the old spark-gap generators produced a sparking from the active electrode, while adjacent to but not in contact with the flesh that caused desication or hemostasis over a fairly wide area of adjacent tissue. Modern solid state electrosurgical systems, when used in the coagulating mode, produce a highly localized hemostasis effect, such that the active electrode must be separately touched to almost all of the many individual "bleeders". This is necessarily a much slower procedure and hence a serious disadvantage.

Only one known essentially solid state electrosurgical system, the "RELIANCE Brand Model ES-47 Electrosurgery System", provides both cut and fulguration currents. However, such system necessarily provides these two currents to separate active electrodes and thereby suffers from the disadvantage that the surgeon must expend extra time in switching active electrodes when sequentially cutting and fulgurating.

SUMMARY OF THE INVENTION

In accordance with the present invention an electrosurgical system, having a solid state generator for providing a cut mode electrosurgical current waveform of RF electric energy having a first voltage amplitude to an active electrode terminal, is adapted by the addition of an apparatus for alternatively providing a fulguration mode current waveform having a second higher voltage amplitude from the generator to the active electrode terminal. This apparatus is a fulguration adaptor including a transformer for enabling the generator to provide a fulguration mode waveform having the second higher voltage amplitude; switching means connected to the transformer for selectively connecting the transformer to the generator for providing said fulguration mode waveform, for disconnecting the transformer from the generator, and for switching off the current from the generator when operated to disconnect the transformer; and a delay circuit connected to the switching means for delaying said disconnection of the transformer until after the current from the generator has been switched off.

The mere addition of a transformer to produce a higher voltage amplitude would reduce the usefulness of the electrosurgical system unless other changes were also made. The system could not be used satisfactorily in the cutting mode at the increased voltage amplitude. Although this problem can be overcome by placing the transformer in only the fulguration circuit and not in the cutting circuit; unfortunately, because of the increased voltage amplitude of the fulguration waveform, switching from the fulguration mode could destroy such switching components as relay contacts due to the high voltage amplitude of the fulguration current. The present invention overcomes this problem by providing a delay of switching from the fulguratin mode until the RF current has been switched off within the generator. The present invention thus provides for the combination of a transformer to increase the output voltage for fulguration and a switching means and delay circuit which can safely accomodate the high voltage amplitude RF currents without imposing dangerous overload upon switching components which were not designed to withstand the high voltage amplitude.

DESCRIPTION OF THE PREFERRED EMBODIMENTS

Figure 1:
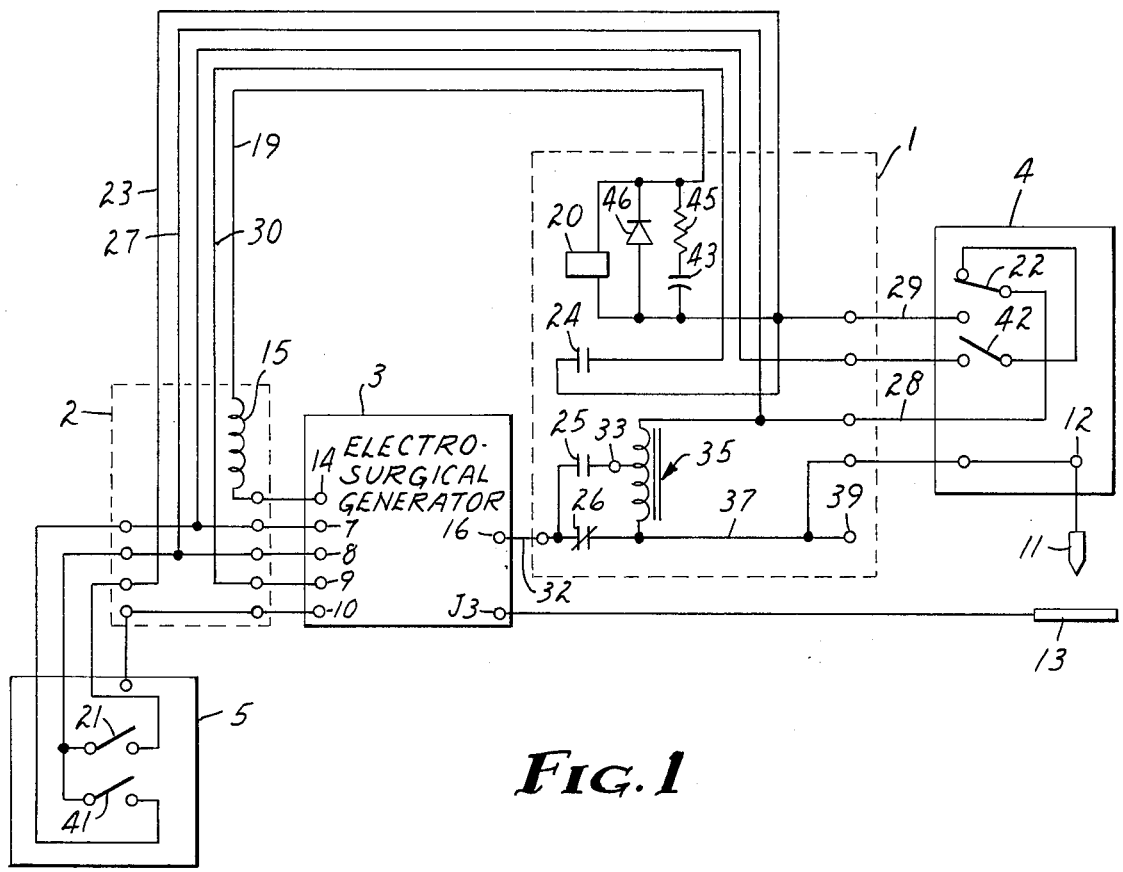
FIG. 1 is a combination block diagram and electrical schematic circuit diagram of a preferred embodiment of the present invention wherein a fulguration adaptor is connected to a prior art solid state electrosurgical generator.

Referring to FIG. 1, a fulguration adapter 1 and a terminal unit 2 are connected to a prior art solid state electrosurgical generator 3, and to a prior art hand controlled switch unit 4 and a prior art foot controlled switch unit 5. The electrosurgical generator 3 is a "3M" Brand MOdel 300 Electrosurgial System, which is described in the Customer Service Manual therefor, particularly FIG. 7-1 thereof. (Said description being incorporated herein by reference thereto.) The reference numerals used herein to designate the terminals of the electrosurgical generator 3 correspond to the terminal designations in said FIG. 7-1 of said Customer Service Manual, a copy of which is being filed in the Patent Office with this application.

Terminal 7 is the "cut" mode relay terminal, at which a circuit may be completed for applying power to actuate the cut mode relay to operate the generator 3 in the cut mode. Terminal 8 is a "common" terminal of a D.C. voltage power supply. Terminal 9 is the "coagulate" mode relay terminal, at which a circuit may be completed for applying power to normally operate the generator 3 in the coagulate mode. Terminal 10 is the chassis ground terminal. Terminal 14 provides a source of positive D.C. voltage. Terminal 16 is the terminal to which the hand control switch unit 4 normally would be connected, the active electrode 11 normally being connected to the active electrode terminal 12 of the hand control unit 4. Terminal J3 is the patient plate (or return electrode) terminal, to which the patient plate 13 is connected.

The hand switch unit 4, and the footswitch unit 5 are used for determining the operating mode, with each having a switch designated "COAG" that is closed for operating in the fulguration mode, and a switch designated "CUT" that is closed for operating in the cut mode. A positive D.C. voltage is applied by line 19 from terminal 14 through inductor 15 to one side of a relay coil 20. The inductor 15 blocks RF energy from being fed back to the D.C. power supply within the generator 3. When either the "COAG" switch 21, of the footswitch unit 5, or the "COAG" switch 22, of the hand switch unit 4, is closed, the D.C. common voltage supply terminal 8 is connected to the other side of the relay coil 20, through line 23, thereby, energizing the relay coil 20, which in turn closes relay contacts 24 and 25 and opens relay contact 26. A circuit to actuate the coagulate mode relay in the generator 3 is thereby completed from the common terminal 8 to the coagulate mode relay terminal 9 either through line 27, line 28, "COAG" switch 22, line 29 relay contacts 24, and line 30, or through "COAG" switch 21, line 23, relay contacts 24, and line 30. After the coagulate mode relay in the generator 3 has been energized a coagulate current is applied to line 32 from the terminal 16. Thus the relay coil 20 first must be energized to complete switching to relay contacts 24, and 25, before the coagulate current is applied to the line 32. This elimintes the problem of trying to switch high voltage RF energy with the relay contacts 25 and 26.

The coagulate current is applied from line 32 through the relay contact 25 to the center tap 33, of transformer 35. The voltage of the RF signal provided at the terminal 16 is doubled by the transformer 35 to provide a waveform capable of fulguration. The fulguration current is carried on line 37, to either the hand control active electrode terminal 12 or to the active electrode terminal 39. When it is desired to change to the cut mode, the "COAG" switch 21 or 22 is opened and then either the "CUT" switch 41 of the footswitch unit 5 or the "CUT" switch 42 of the hand switch unit 4 is closed. When the "COAG" switch 21 or 22 is opened, the coagulate mode relay within the generator 3 is deenergized at the same time, while a capacitor 43 and a resistor 45 act in series to delay the deenergization of the relay coil 20 for a brief additional instant thereby allowing the coagulate mode relay within the generator 3 to be switched off first thus assuring that the high voltage RF energy provided to the line 32 has ceased before the relay contact 25 is switched open and relay contact 26 is again closed. Diode 46 is provided for transient protection.

While it is important that the relay coil 20, remain energized until the coagulate mode relay within the generator 3 is deenergized, it must be deenergized quickly after that so that by the time either the "CUt" switch 41, or the "CUt" switch 42, is activated to cause the cut mode relay within the generator to be energized, the relay contact 25 has opened to remove the transformer 35 voltage gain from the line 37 so that the "CUt" power to the active electrode 11 is not boosted by the transformer 35.

In essence, the fulgurator adapter unit 1 provides a boost in voltage to change a coagulating current to a fulgurating current while leaving the cut mode current unchanged. It provides switching means 20 in combination with a delay circuit 43,45 for assuring that mode switching takes place only after the cessation of a potentially damaging high voltage amplitude RF signal.

It should be understood that the purpose of the fulguration adapter 1 of the present invention is to increase the versatility of solid state equipment such as electrosurgical generator 3, which is already in use in many hospitals so that said equipment 3 may be used more efficiently for an even greater variety of applications. The addition of said fulguration adapter 1 is not intended to be permanent and in fact, the fulguration adapter 1 can be easily removed so that the unit 3 may then be used for its original intended use for cutting and coagulating.

Referring to FIGS. 2 through 7, another preferred embodiment of the present invention is an electrosurgical system which provides for the choice of any one of the modes, cutting, coagulating, blending cutting and coagulation, and fulguration.

Figure 2:
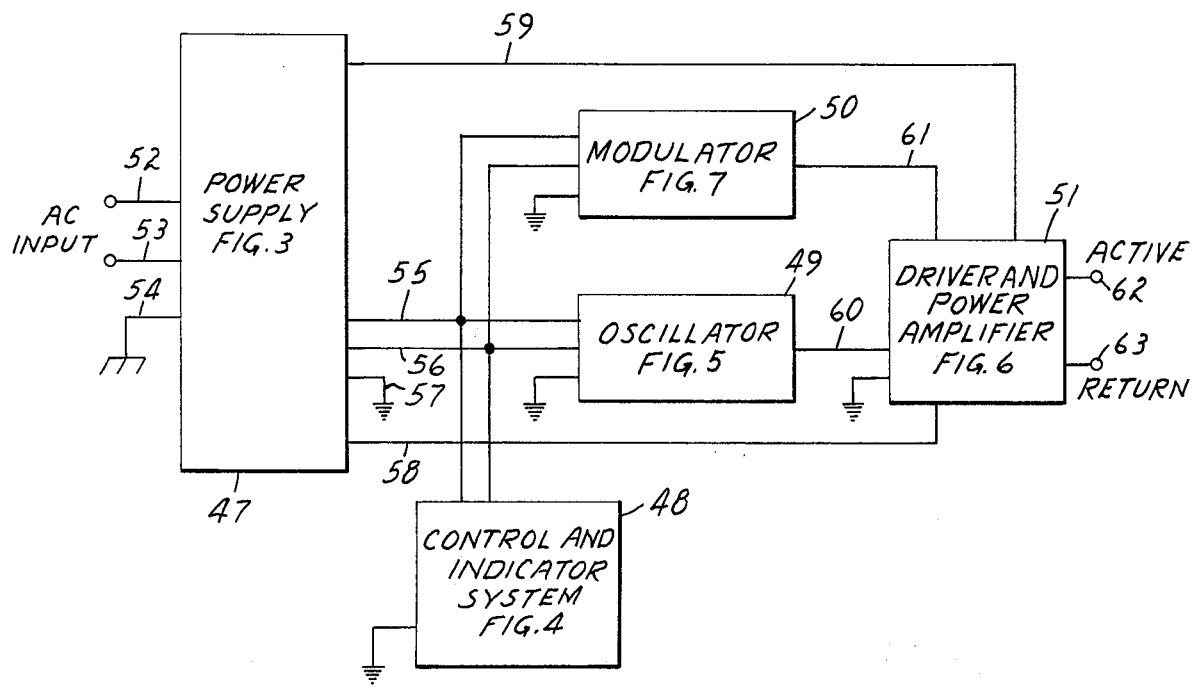
FIG. 2 is a general block diagram of a preferred embodiment of a solid state electrosurgical system in accordance with this invention.

FIG. 2 is a block diagram of this preferred embodiment which includes a power supply 47, a control and indicator system 48, an oscillator 49, a modulator 50, and a driver and power amplifier 51.

The power supply 47 receives normal A.C. input power on lines 52 and 53 with line 54 acting as a chassis ground. D.C. power at various potentials is supplied to the other components on lines 55, 56, 58 and 59 with line 57 acting as a D.C. and signal ground.

The output current of the generator is applied at the active electrode terminal 62, passes through the patient and returns to the generator at the return electrode terminal 63.

Figure 3:
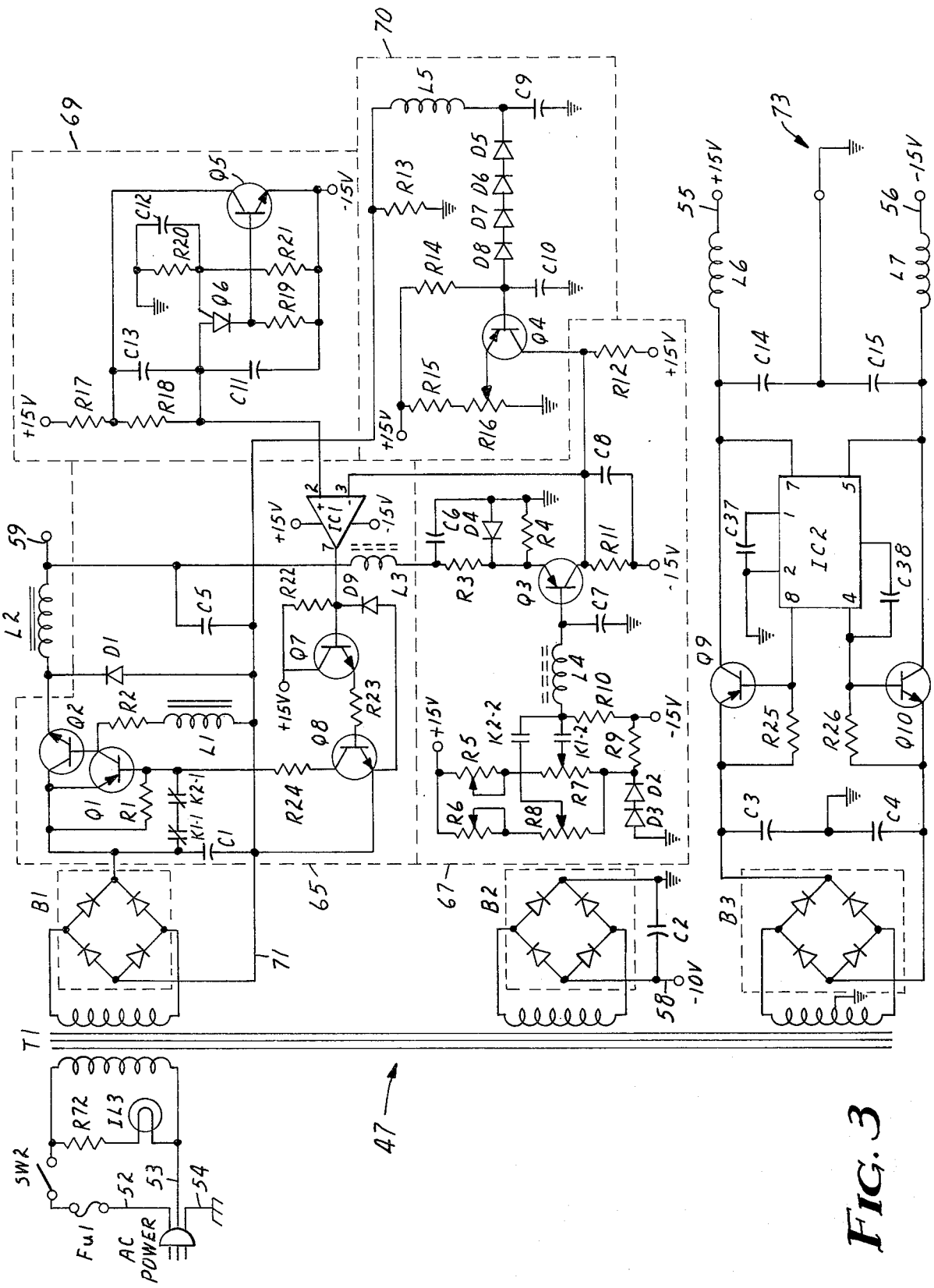
FIG. 3 is an electrical schematic circuit diagram of the power supply indicated in FIG. 2.

FIG. 3 is an electrical schematic circuit diagram of the preferred embodiment of the power supply 47.

A.C. power is supplied to the primary of main power transformer T1 through fuse FU1 and ON/OFF switch SW2. Indicator lamp IL3 indicates the application of A.C. power, with resistor R72 limiting the current to the lamp IL3.

The secondary of the main power transformer T1 is connected to three full-wave diode bridge rectifiers B1, B2 and B3. The 60 Hz component of the rectified voltage is filtered by capacitors C1, C2, C3 and C4. The resultant D.C. voltage from the bridge B1 is supplied to transistors Q1 and Q2 which act together as a series switch in the switching regulator portion 65 of the power supply 47. D.C. voltage goes no further in the circuit until transistors Q1 and Q2 are allowed to turn on by opening either of control relay contacts K1-1 or K2-1. Once either contact K1-1 or K2-1 has opened, the series switch Q1, Q2 will switch on and off at a rate in the range of about 18-20 KHz. Potentials necessary to turn the transistors Q1 and Q2 on and off are supplied at the base of transistor Q1 as described later.

Resistor R1 decreases the time it takes to turn off transistor Q1. Resistor R2 and inductor L1 provide a large negative pulse wih respect to signal ground to decrease the time it takes to turn off transistor Q2. Diode D1 is a flyback diode which provides a current path during the off portion of the switching cycle. Inductor L2 stores energy and provides current on line 59 to the power amplifier 51 during the off portion of the switching cycle of the power regulator 65. Capacitor C5, inductor L3 and capacitor C6 provide additional filtering of the 18-20 KHz components from the D.C. voltage provided on the line 59.

Resistors R3 and R4 act as a voltage divider and provide the proper reference voltage at the emitter of transistor Q3. Diode D4 provides a current path to ground when the base of transistor Q3 is at or below $-1.4$ volts.

A voltage control circuit 67 including transistor Q3 and its associated components controls the level of power supplied to the driver and power amplifier 51. Transistor Q3 forms a common base error amplifier. Resistors R7 and R8, and variable resistors R5 and R6 set the operating power level by controlling the voltage at the base of the transistor Q3. The "CUT" power level is controlled when control relay contact K1-2 is closed and the "COAG" power level is controlled when control relay contact K2-2 is closed. Inductor L4 and capacitor C7 filter out electrical noise picked up on long leads within the generator.

Diodes D2 and D3 and resistor R9 establish a fixed voltage of $-1.4$ volts on the base of the transistor Q3 when variable resistors R7 and R8 are set at zero. Resistor R10 provides base current to transistor Q3 when either of contacts K1-2 and K2-2 is closed. Current through the transistor Q3 develops a voltage across resistor R11 which is applied to pin 3 of integrated circuit IC1. Capacitor C8 filters out noise that otherwise might appear at pin 3 of the integrated circuit IC1. Resistor R12 establishes a minimum voltage level at pin 3 of the integrated circuit IC1 through attachment to the +15 volt D.C. supply.

A sawtooth waveform genertor 69 including a programmable unijunction transistor (PUT) Q6 and its associated components generates a sawtooth waveform which is applied to pin 2 of the integrated circuit IC1. Resistors R17 and R18 and capacitor C11 provide RC timing to establish the frequency of operation of the sawtooth waveform generator 69. Resistor R19 provides a current path for the pulse from the transistor Q6 and develops a base voltage at the transistor Q5 to turn it on with each pulse of PUT Q6. When the transistor Q5 turns on it provides a negative pulse which, in conjunction with capacitor C13, helps turn the PUT Q6 off after each pulse. Resistors R20 and R21 establish the gate voltage at PUT Q6 and hence the firing voltage for the PUT Q6.

The integrated circuit IC1 acts as a comparator. It compares the voltage at pin 3 to the sawtooth voltage at pin 2 and provides a square wave at pin 7. Transistors Q7 and Q8 amplify the square wave from the integrated circuit IC1 and apply it to the base of the transistor Q1 to turn the latter on and off. Resistor R22 pulls up the voltage level at pin 7 during the positive portion of the square wave as the integrated circuit IC1 does not have an active pull up means. Diode D9 aids in lowering the voltage level at the emitter of transistor Q7 during the negative portion of the square wave through the active pull down of the integrated circuit IC1. Resistor R23 provides base drive for transistor Q8. Resistor R24 provides base drive for the transistor Q1.

Transistor Q4 and its associated components form the current limiting portion 70 of the power supply 47. All load current flows through resistor R13 and generates a voltage proportional to current through line 71. This voltage is applied, less four diode drops, at the base of the transistor Q4. Resistors R15 and R16 establish the emitter voltage of the transistor Q4 and thus the point at which the transistor Q4 turns on. When the voltage at the base of the transistor Q4 is sufficiently negative (i.e. the load current is sufficiently large) the transistor Q4 will turn on and the high resulting voltage at pin 3 of the integrated circuit IC1 will limit the on time of the square wave at pin 7, thus limiting the load current. Inductor L5, and capacitors C9 and C10 are for noise filtering. Resistor R14 increases the rate of transistor Q4 base pull up. Diodes D5, D6, D7 and D8 provide a 2.8 volt drop to prevent premature turn on of the transistor Q4.

Figure 6:
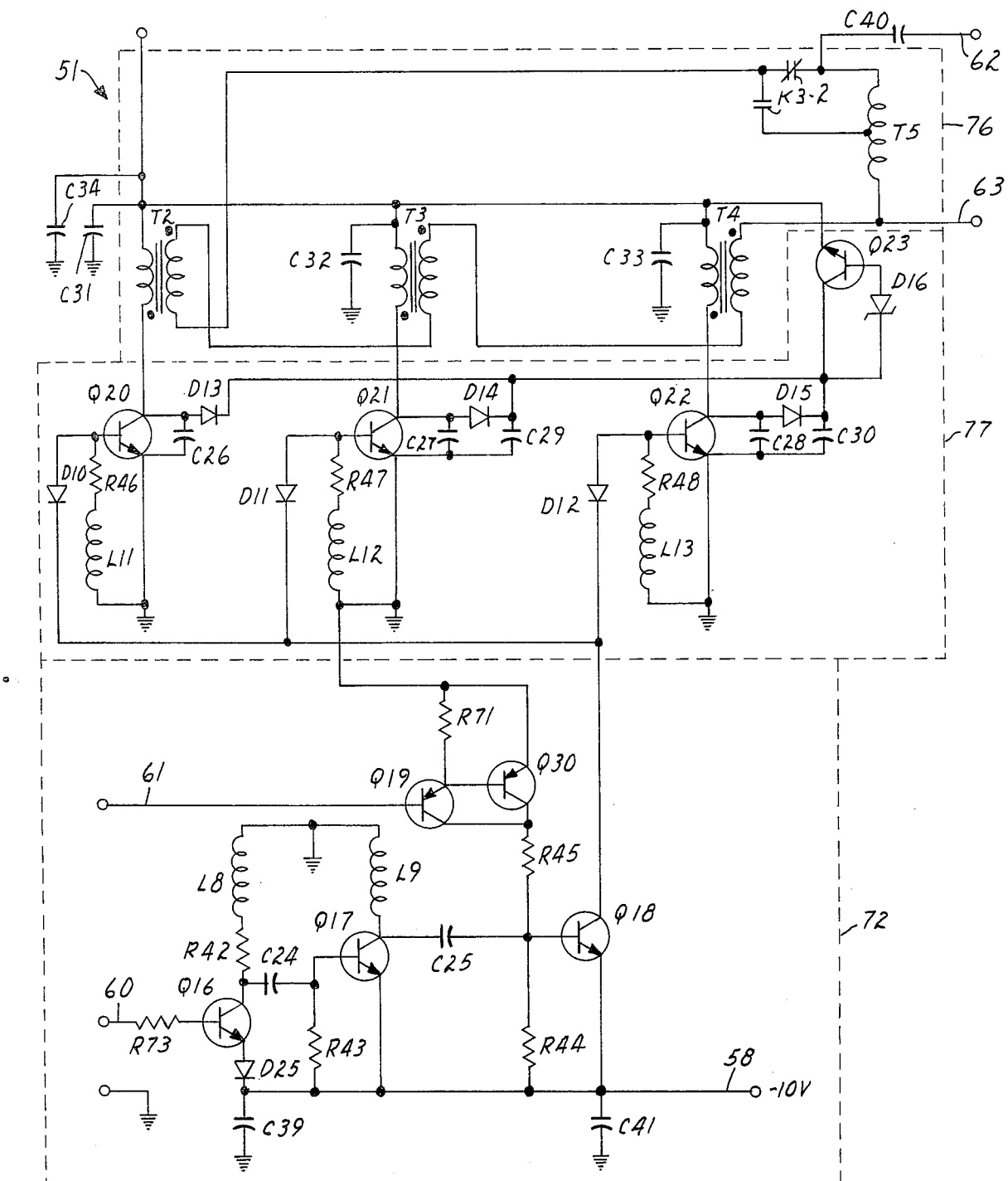
FIG. 6 is an electrical shematic circuit diagram of the driver and power amplifier indicated in FIG. 2.

Diode bridge B2 provides −10 volts D.C. on line 58 to the driver 72 in the driver and power amplifier 51 (FIG. 6). Capacitor C2 is for filtering out 60 Hz components.

Diode bridge B3 provides voltage for the ± 15 volt section 73 of the power supply 47. Capacitors C3 and C4 are for filtering out 60 Hz components. Integrated circuit IC2 and its associated components provide ± 15 volts D.C. regulated voltage to other sections of the electrosurgical generator. Transistors Q9 and Q10 with resistors R25 and R26 amplify the current supplied by the integrated circuit IC2 since it cannot supply sufficient regulated current alone. Capacitors C37 and C38 are provided for proper operation of the integrated circuit IC2. Capacitors C14 and C15, and inductors L6 and L7 provide filtering to keep electrical noise on the ±15 volt lines from getting back into the integrated circuit IC2.

Figure 4:
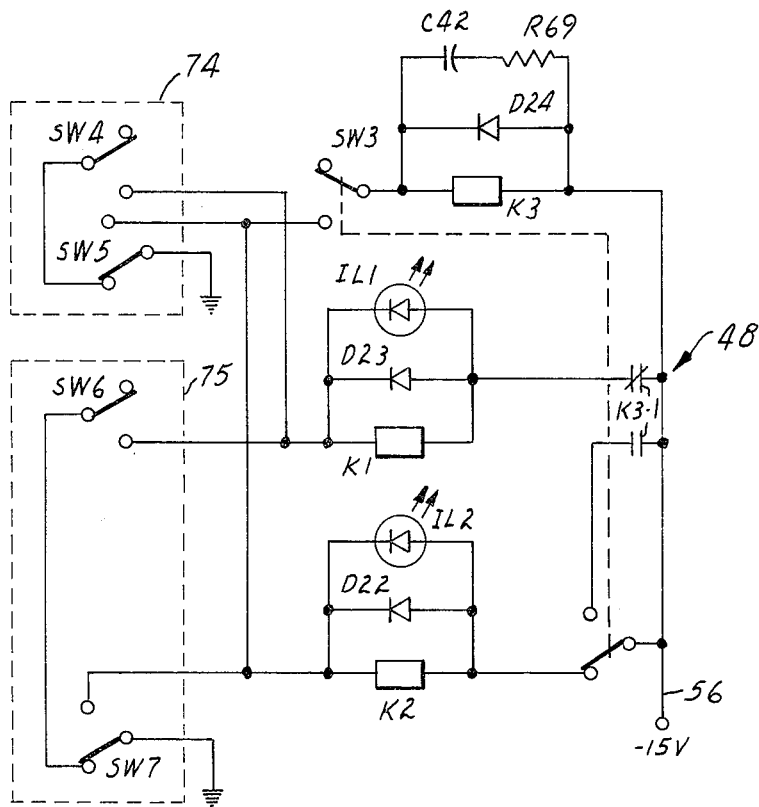
FIG. 4 is an electrical schematic circuit diagram of the control and indicator system indicated in FIG. 2.

Referring to FIG. 4 the hand controlled switch unit 74 and foot controlled switch 75 are external to the electrosurgical generator. Switches SW4 and SW6 control the actuation of "CUT" control relay coil K1. Switches SW5 and SW7 control the actuation of "COAG" relay coil K2. When either coil K1 or coil K2 is actuated, the appropriate indicator lamp, IL1 or IL2, lights. Diodes D22 and D23 are for transient suppression.

Switch SW3 actuates "FULGURATE" control relay coil K3 which allows the application of a waveform with higher voltage than the coagulation waveform at the active electrode terminal 62 for fulguration procedures. Diode D24 is for transient suppression.

Capacitor C42 and resistor R69 delay deenergization of the relay coil K3 until generator current has been switched off by the resultant deenergization of relay coil K2 to prevent switching of RF energy through relay contacts K3-2 in the power transformer portion 76 of the driver and power amplifier 51 (FIG. 6), thereby preventing damage to the relay contacts K3-2 upon the opening of the "COAG" switch SW5 and SW7. Relay contact K3-1 enables energization of the relay coil K2 and prevents energization of the relay coil K1 during fulguration.

Figure 5:
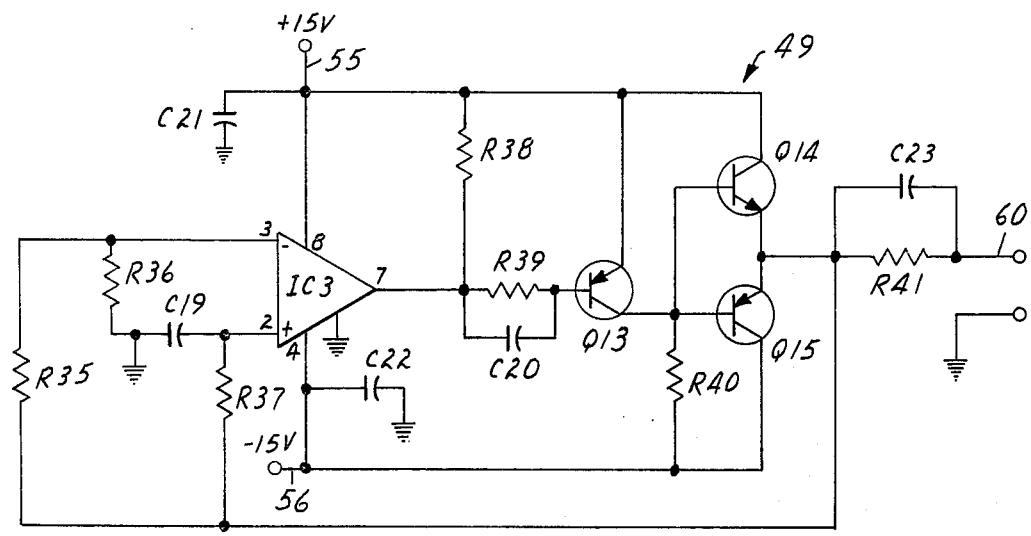
FIG. 5 is an electrical schematic circuit diagram of the oscillator indicated in FIG. 2.

Referring to FIG. 5, integrated circuit IC3 and its associated components form the basic oscillator which oscillates at 1 megahertz. The waveform generated on line 60 is a square wave.

The waveform at pin 3 of the integrated circuit IC3 is a square wave. The square wave voltage amplitude is set by resistors R35 and R36 which act as a voltage divider. The waveform at pin 2 of the integrated circuit IC3 is a typical RC charge-discharge waveform. Capacitor C19 and resistor R37 establish the charge and discharge time. The integrated circuit IC3 compares the voltages at pin 2 and 3 and generates a square wave at pin 7. Transistors Q13, Q14 and Q15 amplify the square wave so that sufficient drive current can be supplied on line 60 to the driver 72 (FIG. 6).

Capacitors C21 and C22 are for noise filtering. Resistor R38 pulls pin 7 of the integrated circuit IC3 high during the positive portion of the square wave at pin 3 as as the integrated circuit IC3 does not have an active pull up means. Resistor R39 limits base current to the transistor Q13. Capacitor C20 decreases turn on time for transistor Q13. Resistor R40 pulls the collector of transistor Q13 to a low voltage level during the negative portion of the square wave at pin 7. Resistor R41 limits base current to transistor Q16 in the driver 72 (FIG. 6). Capacitor C23 decreases turn on time for the transistor Q16.

Referring to the driver 72 as shown in FIG. 6, transistors Q16, Q17 and Q18 and their associated components amplify the 1 megahertz square wave sigal on line 60 from the oscillator 49 (FIG. 5) so that sufficient power is obtained to drive the power amplifier 77. Inductor L8 and resistor R42 provide a negative pulse when the transistor Q16 turns on to decrease transistor Q17 turn off time. Capacitor C24 couples the negative pulses and signals from the transistor Q16 to the transistor Q17. Resistor R43 provides a discharge path for capacitor C24. Inductor L9 provides a negative pulse when the transistor Q17 turns on to decrease transistor Q18 turn off time. Capacitor C25 couples the negative pulses, and signals from the transistor Q17, to the transistor Q18.

Resistor R44 provides a discharge path for capacitor C25. Capacitor C39 provides noise by-pass filtering. Capacitor C41 filters out 60 Hz components on the line 58. Resistor R73 provides transmission line matching impedance on line 60. Diode 25 prevents emitter to base breakdown of the transistor Q16.

Figure 7:
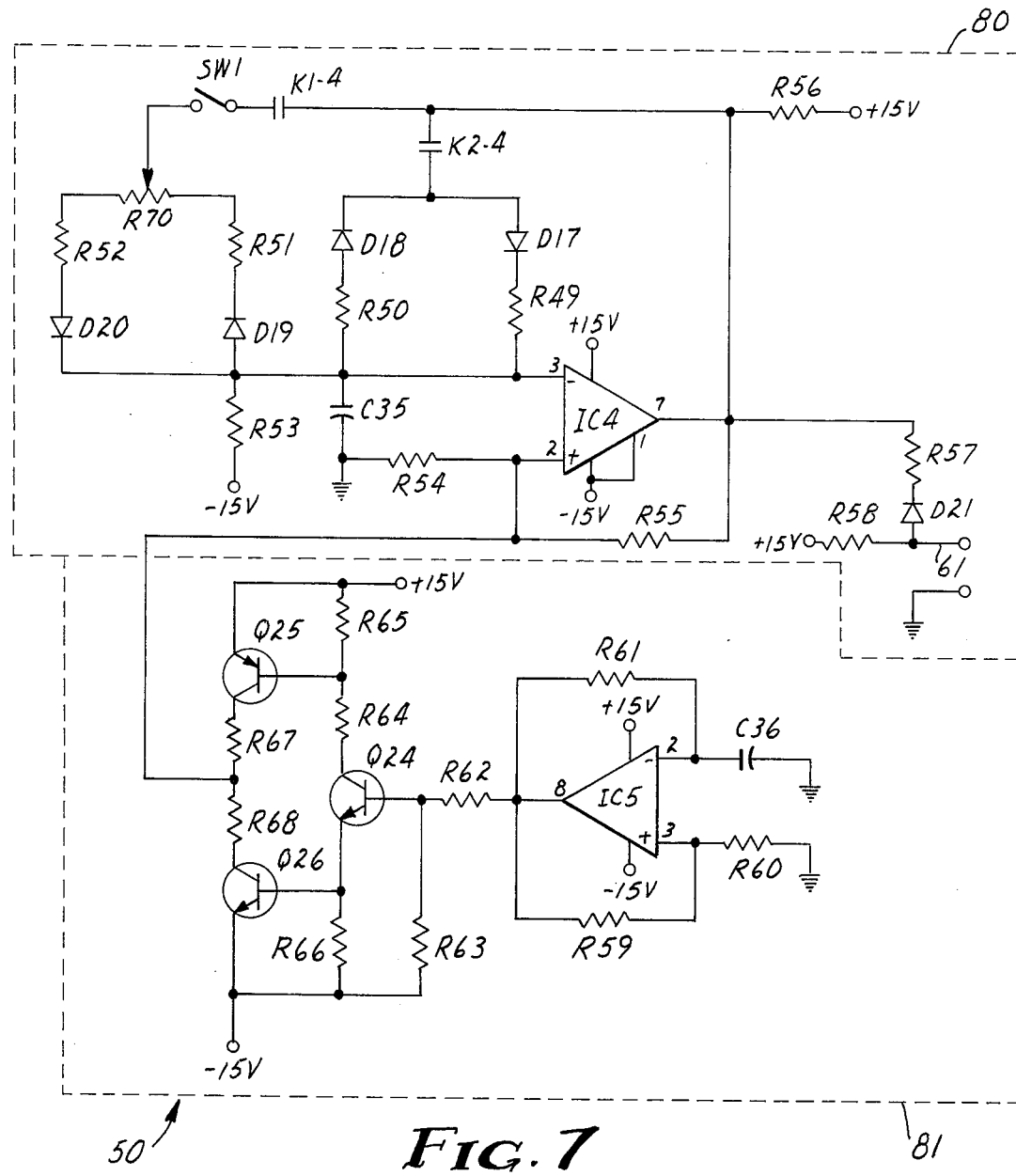
FIG. 7 is an electrical schematic circuit diagram of the modulator indicated in FIG. 2.

Transistors Q19 and Q30 with resistor R72 form a Darlington amplifier which is controlled by the modulator 50 (FIG. 7). When transistors Q19 and Q30 are on, transistor Q18 is held on and ignores any signals from the transistor Q17. Resistor R45 limits base current to the transistor Q18. When transistors Q19 and Q30 are off, the transistor Q18 is driven on and off at the main oscillator frequency of 1 megahertz by the transistor Q17 to drive the power amplifier 77. The waveform from the modulator 50 interupts the main oscillator waveform, amplified by the driver 72, at a frequency of about 15 KHz to provide pulses of RF energy to the power amplifier 77.

Transistors Q20, Q21 and Q22 and their associated components form the power amplifier 77. When Q19, Q30 and Q18 are on, current flows through inductors L11, L12, and L13, resistors R46, R47, and R48, and diodes D10, D11 and D12. This stores energy in inductors L11, L12 and L13. Power amplifier transistors Q20, Q21 and Q22 then are off.

When Q19 and Q30 are off, the charge stored in inductors L11, L12, and L13 is dumped through the transistors Q20, Q21 and Q22 to turn them on.

Resistors R46, R47 and R48 determine the level of charge in the inductors L11, L12 and L13 and help keep the current constant when turning the transistors Q20, Q21 and Q22 on. Capacitors C26, C27 and C28 help limit the rate of current change when turning off the transistors Q20, Q21 and Q22. Diodes D13, D14, D15 and D16, and transistor Q23 clamp the voltage at the collectors of the transistors Q20, Q21 and Q22 at a low enough level to avoid transistor damage.

The voltage clamp is necessary because of the spike caused when transistors Q20, Q21 and Q22 turn off. Capacitors C29 and C30 slow down the spike to allow the slow reacting clamp to respond.

Transformers T2, T3 and T4 increase the output voltages of transistors Q20, Q21 and Q22 to a higher level. The secondary windings of the transformers T2, T3 and T4 are connected in series addition to add and apply these increased voltage to the active and return electrode terminals 62 and 63. Transformer T5 provides higher output voltage for fulguration when relay contacts K3-1 and K3-2 are closed. Capacitor C40 eliminates D.C. currents in the patient circuit between terminals 62 and 63.

Capacitors C31, C32 and C33 cancel out the effect of transformer T2, T3 and T4 lead inductances which act like leakage inductors. Capacitor C34 stabilizes the voltage to the power amplifier.

Referring to FIG. 7, integrated circuit IC4 and its associated components form an oscillator 80 similar to the main 1 MHz oscillator 49 but operating at a lower frequency of 15 KHz. Resistors R54 and R55 form a voltage divider to set the maximum voltage at pin 2 of the integrated circuit IC4. Resistor R56 is for current limiting.

Relay contact K2-4 controls the coagulation portion of the modulator 50. When contact K2-4 is closed, capacitor C35 is charged through diode D17 and resistor R49 which establishes the on time for the modulator signal. Capacitor C35 discharges through diode D18 and resistor R50 which establishes the modulator off time.

Relay contact K1-4 controls the cut with variable hemostasis (blend) portion of the modulator 50. When relay contact K1-4 and switch SW1 are closed, capacitor C35 is charged through diode D20, resistor R52 and a portion of resistor R70 which establish the on time for the modulator. C35 discharges through diode D19, resistor R51 and a portion of R70 which establish the modulator off time. Resistor R70 controls the proportion of on time to off time. With switch SW1 open, and relay contact K2-4 open, resistor R53 disables the modulator.

Resistors R57 and R58 and diode D21 assure proper turn on and turn off of transistors Q19 and Q30 which respond to the modulator waveform to modulate the driver waveform.

Integrated circuit IC5 and its associated components form an oscillator 81 which affects the modulator output waveform provided on line 61 to make it essentially non-periodic. It is believed that such non-periodicity may enhance coagulation. Resistors R59, R60 and R61 and capacitor C36 establish the oscillator 81 operating fequency at 1 KHz. Transistors Q24, Q25 and Q26 with resistors R62, R63, R64, R65 and R66 form a switching means to switch resistors R67 and R68 across resistor R54 to thereby alter the modulator 50 operating frequency at a rate controlled by the integrated circuit IC5.

Component values and identification for a preferred embodiment of the electrosurgical generator shown in FIG. 2–7 are as follows:

Resistors
(½ watt unless specified otherwise)

| | | | |
|---|---|---|---|
| R1 | 10 ohms | R29 | 47 ohms |
| R2 | 50 ohms 25 watts | R30 | 470 ohms |
| R3 | 3.3 Kohms | R31 | 150 Kohms |
| R4 | 1 Kohm | R32 | 220 Kohms |
| R5 | 1 Kohm variable | R33 | 1 Kohm variable |
| R6 | 1 Kohm variable | R34 | 10 ohms |
| R7 | 1 Kohm variable | R35 | 4.7 Kohms |
| R8 | 1 Kohm variable | R36 | 1 Kohm |
| R9 | 470 ohms | R37 | 4.7 Kohms |
| R10 | 10 Kohms | R38 | 1.5 Kohm |
| R11 | 10 Kohms | R39 | 1.5 Kohm |
| R12 | 220 Kohms | R40 | 270 ohms 2 watts |
| R13 | .1 ohm 50 watts | R41 | 100 ohms 2 watts |
| R14 | 4.7 Kohms | R42 | 27 ohms 2 watts |
| R15 | 1 Kohm | R43 | 15 ohms 1 watt |
| R16 | 250 ohms variable | R44 | 10 ohms 2 watts |
| R17 | 22 Kohms | R45 | 4.7 ohms 2 watts |
| R18 | 2.2 Kohms | R46 | 1 ohm 20 watts |
| R19 | 27 ohms | R47 | 1 ohm 20 watts |
| R20 | 47 ohms | R48 | 1 ohm 20 watts |
| R21 | 220 ohms | R49 | 82 Kohms |
| R22 | 4.7 Kohms | R50 | 330 Kohms |
| R23 | 1 Kohm | R51 | 100 Kohms |
| R24 | 150 ohms 50 watts | R52 | 47 Kohms |
| R25 | 47 ohms | R53 | 10 Megohms |
| R26 | 47 ohms | R54 | 4.7 Kohms |
| R27 | 1 Kohm | R55 | 10 Kohms |
| R28 | 2.2 Kohms | R56 | 680 ohms 1 watt |
| R57 | 150 ohms 1 watt | | |
| R58 | 4.7 Kohms | | |
| R59 | 5.6 Kohms | | |
| R60 | 10 Kohms | | |
| R61 | 10 Kohms | | |
| R62 | 10 Kohms | | |
| R63 | 1 Kohm | | |
| R64 | 2.2 Kohms | | |
| R65 | 470 ohms | | |
| R66 | 470 ohms | | |
| R67 | 100 Kohms | | |
| R68 | 100 Kohms | | |
| R69 | 330 ohms | | |
| R70 | 250 Kohms variable | | |
| R71 | 100 ohms | | |
| R72 | 33 Kohms | | |
| R73 | 75 ohms | | |

Capacitors

| | | | |
|---|---|---|---|
| C1 | 14,000 microfarads | C12 | .1 microfarad |
| C2 | 82,000 microfarads | C13 | .1 microfarad |
| C3 | 1100 microfarads | C14 | 100 microfarads |
| C4 | 1100 microfarads | C15 | 100 microfarads |
| C5 | 4700 microfarads | C16 | .1 microfarad |
| C6 | .1 microfarad | C17 | .0039 microfarad |
| C7 | .1 microfarad | C18 | 25 microfarads |
| C8 | .01 microfarad | C19 | 220 picofarads |
| C9 | .1 microfarad | C20 | 350 picofarads |
| C10 | .1 microfarad | C21 | .1 microfarad |
| C11 | .0047 microfarad | C22 | .1 microfarad |
| C23 | 360 picofarads | C33 | 1 microfarad |
| C24 | .01 microfarad | C34 | 1150 microfarads |
| C25 | .1 microfarad | C35 | 220 picofarads |
| C26 | 2200 picofarads | C36 | .01 microfarad |
| C27 | 2200 picofarads | C37 | .1 microfarad |
| C28 | 2200 picofarads | C38 | .1 microfarad |
| C29 | 1 microfarad | C39 | .01 microfarad |
| C30 | 1 microfarad | C40 | .05 microfarad |
| C31 | 1 microfarad | C41 | 125 microfarads |
| C32 | 1 microfarad | C42 | 15 microfarads |

Inductors

| | | | |
|---|---|---|---|
| L1 | .7 millihenries | L7 | 1 microhenries |
| L2 | 1 millihenries | L8 | 1 microhenries |
| L3 | 100 microhenries | L9 | 1 microhenries |
| L4 | 100 microhenries | L10 | |
| L5 | 1 microhenries | L11 | 1 microhenries |
| L6 | 1 microhenries | L12 | 1 microhenries |
| | | L13 | 1 microhenries |
| | | L14 | |

Integrated Circuits

| | |
|---|---|
| IC1 | LM311 |
| IC2 | RC4195 |
| IC3 | LM306H |
| IC4 | LM311 |
| IC5 | 741 |

Bridge Rectifiers

| | |
|---|---|
| B1 | 2502B1L Int. Rectifier |
| B2 | 2502B1L Int. Rectifier |
| B3 | MDA920A-3 |

Relays

| | |
|---|---|
| K1 | Guardian 1315-4C-12VDC |
| K2 | Guardian 1315-4C-12VDC |
| K3 | C.P. Clare HGS2MT51111J00 |

Diodes

| | | | |
|---|---|---|---|
| D1 | S2110 | D14 | UES204 |
| D2 | 1N914 | D15 | UES204 |
| D3 | 1N914 | D16 | 1N4759 |
| D4 | 1N914 | D17 | 1N914 |
| D5 | 1N914 | D18 | 1N914 |
| D6 | 1N914 | D19 | 1N914 |
| D7 | 1N914 | D20 | 1N914 |
| D8 | 1N914 | D21 | 1N914 |
| D9 | 1N914 | D22 | 1N914 |
| D10 | UES201 | D23 | 1N914 |
| D11 | UES201 | D24 | 1N914 |
| D12 | UES201 | D25 | 1N914 |
| D13 | UES204 | | |

Transistors

| | | | | | |
|---|---|---|---|---|---|
| Q1 | MJ491 | Q13 | 2N4402 | Q25 | 2N4402 |

-continued

| | | | | | |
|---|---|---|---|---|---|
| Q2 | 2N3772 | Q14 | 2N4400 | Q26 | 2N4400 |
| Q3 | 2N4402 | Q15 | 2N4402 | Q27 | |
| Q4 | 2N4402 | Q16 | 2N4401 | Q28 | |
| Q5 | 2N4400 | Q17 | 2N5430 | Q29 | |
| Q6 | 2N6028 | Q18 | 2N6275 | Q30 | 2N4402 |
| Q7 | 2N4400 | Q19 | 2N5194 | | |
| Q8 | 2N4922 | Q20 | 2N6275 | | |
| Q9 | MJ491 | Q21 | 2N6275 | | |
| Q10 | 2N3055 | Q22 | 2N6275 | | |
| Q11 | 2N4922 | Q23 | 2N3772 | | |
| Q12 | 2N6028 | Q24 | 2N4400 | | |

What is claimed is:

1. A fulguration adaptor for enabling an electrosurgical system including a solid state generator for providing a cut mode electrosurgical current waveform of RF electric energy having a first voltage amplitude to an active electrode terminal to which an electrosurgical instrument is connected during use of the system, to alternatively provide a fulguration mode current waveform from the generator to the active electrode terminal, said adaptor comprising transformer means for enabling the generator to provide a fulguration mode waveform having a second higher voltage amplitude;

switching means connected to the transformer means for selectively connecting the transformer means to the generator for providing said fulguration mode waveform, for disconnecting the transformer means from the generator, and for switching off the current from the generator when operated to disconnect the transformer means; and delay circuit means connected to the switching means for delaying said disconnection of the transformer means until after the current from the generator has been switched off.

2. An electrosurgical system having a solid state generator for providing a first voltage amplitude cut mode electrosurgical current waveform of RF electric energy to an active electrode terminal to which an electrosurgical instrument is connected during use of the system, the improvement comprising means for alternatively providing a fulguration mode current waveform from the generator to the active electrode terminal, which means includes:

transformer means for enabling the generator to provide a fulguration mode waveform having a second higher voltage amplitude;

switching means connected to the transformer means for selectively connecting the transformer means to the generator for providing said fulguration mode waveform, for disconnecting the transformer means from the generator, and for switching off the current from the generator when operated to disconnect the transformer means; and delay circuit means connected to the switching means for delaying said disconnection of the transformer means until after the current from the generator has been switched off.

3. An electrosurgical system having a solid state generator for providing cut mode and coagulation mode electrosurgical current waveforms of RF electric energy having a relatively low voltage amplitude to an active electrode terminal to which an electrosurgical instrument is connected during use of said system, the improvement comprising means for alternatively providing a fulguration mode current waveform from the generator to the active electrode terminal, said fulguration mode providing means including transformer means for changing the coagulation mode waveform to provide a fulguration mode waveform having a second higher voltage amplitude;

switching means connected to the transformer means for selectively connecting the transformer means to the generator for providing said fulguration mode waveform, for disconnecting the transformer means from the generator, and for switching off the current from the generator when operated to disconnect the transformer means; and delay circuit means connected to the switching means for delaying said disconnection of the transformer means until after the current from the generator has been switched off.

* * * * *

UNITED STATES PATENT OFFICE
CERTIFICATE OF CORRECTION

Patent No. 3,952,748　　　　Dated April 27, 1976

Inventor(s)　Paul Kaliher et al.

It is certified that error appears in the above-identified patent and that said Letters Patent are hereby corrected as shown below:

Column 3, line 5, change "fulguratin" to --- fulguration ---;

Column 3, line 10, change "accomodate" to --- accommodate ---;

Column 3, line 42, change "MOdel" to --- Model ---.

Column 4, lines 53, 54 and 58, change "CUt" to --- CUT ---.

Column 6, line 23, change "genertor" to --- generator ---.

Column 7, line 41, change "and" to --- or ---.

Column 8, line 25, change "R 72" to --- R 71 ---.

Signed and Sealed this

Twenty-first Day of September 1976

[SEAL]

*Attest:*

RUTH C. MASON
*Attesting Officer*

C. MARSHALL DANN
*Commissioner of Patents and Trademarks*